(12) United States Patent
King et al.

(10) Patent No.: US 11,905,627 B2
(45) Date of Patent: Feb. 20, 2024

(54) SYSTEMS FOR MAINTAINING MOISTURE IN A TEXTILE ELECTRODE

(71) Applicant: Propel, LLC, Pawtucket, RI (US)

(72) Inventors: Clare King, Providence, RI (US); Anjali Khemani, Providence, RI (US); Birgit Leitner, Providence, RI (US)

(73) Assignee: Propel, LLC, Pawtucket, RI (US)

( * ) Notice: Subject to any disclaimer, the term of this patent is extended or adjusted under 35 U.S.C. 154(b) by 526 days.

(21) Appl. No.: 16/845,781

(22) Filed: Apr. 10, 2020

(65) Prior Publication Data
US 2020/0323491 A1    Oct. 15, 2020

Related U.S. Application Data

(60) Provisional application No. 62/832,101, filed on Apr. 10, 2019, provisional application No. 62/832,104, (Continued)

(51) Int. Cl.
*A61B 5/00* (2006.01)
*A61B 5/053* (2021.01)
(Continued)

(52) U.S. Cl.
CPC .............. *D02G 3/36* (2013.01); *D02G 3/045* (2013.01); *D02G 3/047* (2013.01); *D02G 3/12* (2013.01);
(Continued)

(58) Field of Classification Search
None
See application file for complete search history.

(56) References Cited

U.S. PATENT DOCUMENTS

| 3,472,289 A | 10/1969 | Riordan et al. |
| 4,262,480 A | 4/1981 | Wasserman et al. |

(Continued)

FOREIGN PATENT DOCUMENTS

| CN | 105209673 A | 12/2015 |
| EP | 0458343 A1 | 11/1991 |

(Continued)

OTHER PUBLICATIONS

U.S. Appl. No. 16/845,772, filed April 10, 2020, Knitted Textiles with Conductive Traces of a Hybrid Yarn and Methods of Knitting the Same.

(Continued)

*Primary Examiner* — Shawn Mckinnon
(74) *Attorney, Agent, or Firm* — Nutter McClennen & Fish LLP

(57) ABSTRACT

A system for continuously humidifying a textile electrode during its use by a human is disclosed. The electrode can be part of a garment or textile where the textile electrode is positioned against the skin. A reservoir positioned against the electrode and opposite the user's skin can be made from a material with hydrophilic and hydrophobic properties, such as natural wool or a skincore material. The reservoir receives and retains moisture from the user's skin through the electrode, as well as from a pre-wetting of the exposed user-facing side of the electrode. A seal can surround the reservoir and the electrode, with the seal extending beyond electrode. The seal can be a patch with heat activated adhesive at the edge to flow the textile to form a moisture barrier around the electrode. An electrical contact on the electrode can connect conductive wires from outside the seal to the electrode.

22 Claims, 11 Drawing Sheets

Related U.S. Application Data filed on Apr. 10, 2019, provisional application No. 62/832,098, filed on Apr. 10, 2019.

(51) Int. Cl.
| | |
|---|---|
| *D02G 3/44* | (2006.01) |
| *D04B 1/12* | (2006.01) |
| *D02G 3/36* | (2006.01) |
| *D02G 3/04* | (2006.01) |
| *D02G 3/12* | (2006.01) |
| *D03D 1/00* | (2006.01) |
| *H05K 1/03* | (2006.01) |
| *A61B 5/25* | (2021.01) |
| *A61B 5/27* | (2021.01) |

(52) U.S. Cl.
CPC ............ *D02G 3/441* (2013.01); *D02G 3/443* (2013.01); *A61B 5/25* (2021.01); *A61B 5/27* (2021.01); *A61B 5/6804* (2013.01); *A61B 2562/14* (2013.01); *D03D 1/0088* (2013.01); *D04B 1/12* (2013.01); *D04B 1/126* (2013.01); *D10B 2211/02* (2013.01); *D10B 2401/16* (2013.01); *D10B 2403/02431* (2013.01); *D10B 2501/00* (2013.01); *H05K 1/038* (2013.01); *H05K 2201/0281* (2013.01)

(56) References Cited

U.S. PATENT DOCUMENTS

| | | | |
|---|---|---|---|
| 4,640,689 | A | 2/1987 | Sibalis |
| 4,868,580 | A | 9/1989 | Wade |
| 4,926,910 | A | 5/1990 | Wade |
| 5,193,607 | A | 3/1993 | Demukai et al. |
| 5,288,289 | A | 2/1994 | Haak et al. |
| 5,927,060 | A | 7/1999 | Watson |
| 6,941,775 | B2 | 9/2005 | Sharma |
| 7,133,227 | B2 | 11/2006 | Chiang et al. |
| 7,308,294 | B2 | 12/2007 | Hassonjee et al. |
| 7,319,895 | B2 | 1/2008 | Klefstad-Sillonville et al. |
| 7,592,276 | B2 | 9/2009 | Hill et al. |
| 7,779,656 | B2 | 8/2010 | Dias et al. |
| 8,060,175 | B2 | 11/2011 | Rowlandson et al. |
| 8,214,008 | B2 | 7/2012 | Hassonjee et al. |
| 8,283,563 | B2 | 10/2012 | Harris et al. |
| 8,505,474 | B2 | 8/2013 | Kang et al. |
| 8,934,957 | B2 | 1/2015 | Dias et al. |
| 9,186,092 | B2 | 11/2015 | Mestrovic et al. |
| 9,388,514 | B2 | 7/2016 | Roh |
| 9,801,583 | B2 | 10/2017 | Derchak et al. |
| 10,011,925 | B2 | 7/2018 | Kurahashi et al. |
| 10,070,815 | B2 | 9/2018 | Shoshani et al. |
| 10,144,193 | B2 | 12/2018 | Haraikawa et al. |
| 10,155,274 | B2 | 12/2018 | Robinson et al. |
| 10,299,520 | B1 | 5/2019 | Shaffer et al. |
| 10,301,751 | B2 | 5/2019 | Dias et al. |
| 10,448,680 | B2 | 10/2019 | Howland |
| 10,462,898 | B2 | 10/2019 | Longinotti-Buitoni et al. |
| 10,480,104 | B2 | 11/2019 | Fu et al. |
| 10,480,106 | B2 | 11/2019 | Krajewski et al. |
| 10,485,103 | B1 | 11/2019 | Sunshine et al. |
| 10,492,302 | B2 | 11/2019 | Karagozler et al. |
| 10,503,339 | B2 | 12/2019 | Karagozler |
| 10,519,575 | B2 | 12/2019 | Thompson et al. |
| 10,577,732 | B1 | 3/2020 | Podhajny et al. |
| 10,754,486 | B2 | 8/2020 | Cobanoglu et al. |
| 2004/0057176 | A1 | 3/2004 | Dhawan et al. |
| 2005/0034485 | A1 | 2/2005 | Klefstad-Sillonville et al. |
| 2005/0231207 | A1 | 10/2005 | Goldwater et al. |
| 2006/0218778 | A1 | 10/2006 | Jawahar et al. |
| 2007/0083096 | A1 | 4/2007 | Paradiso |
| 2007/0281155 | A1 | 12/2007 | Tao et al. |
| 2008/0044652 | A1 | 2/2008 | Krans et al. |
| 2008/0282665 | A1 | 11/2008 | Speleers |
| 2009/0018428 | A1 | 1/2009 | Dias et al. |
| 2010/0084179 | A1 | 4/2010 | Harris et al. |
| 2010/0199901 | A1 | 8/2010 | Kang et al. |
| 2011/0132040 | A1 | 6/2011 | Jahn et al. |
| 2012/0100386 | A1 | 4/2012 | Honma et al. |
| 2012/0225275 | A1 | 9/2012 | Honma et al. |
| 2013/0172722 | A1 | 7/2013 | Ninane et al. |
| 2013/0302605 | A1 | 11/2013 | Yang et al. |
| 2014/0039292 | A1* | 2/2014 | Su .................... A61B 5/276 600/372 |
| 2014/0223650 | A1 | 8/2014 | Hines et al. |
| 2014/0262478 | A1 | 9/2014 | Harris et al. |
| 2014/0363656 | A1 | 12/2014 | Kunisada et al. |
| 2015/0087925 | A1 | 3/2015 | Pedley et al. |
| 2015/0297135 | A1 | 10/2015 | Shoshani et al. |
| 2016/0018274 | A1 | 1/2016 | Seitz |
| 2016/0145776 | A1 | 5/2016 | Roh |
| 2016/0284436 | A1 | 9/2016 | Fukuhara et al. |
| 2017/0073172 | A1 | 3/2017 | Kuijpers et al. |
| 2017/0079348 | A1 | 3/2017 | Chahine et al. |
| 2017/0107647 | A1 | 4/2017 | Riethmuller et al. |
| 2017/0232538 | A1 | 8/2017 | Robinson et al. |
| 2017/0275789 | A1 | 9/2017 | Dias et al. |
| 2018/0042551 | A1 | 2/2018 | Gouthez et al. |
| 2018/0073172 | A1 | 3/2018 | Kurahashi et al. |
| 2018/0085060 | A1 | 3/2018 | Shoshani et al. |
| 2018/0087191 | A1 | 3/2018 | Threlkeld |
| 2018/0151795 | A1 | 5/2018 | Cobanoglu et al. |
| 2018/0195210 | A1 | 7/2018 | Sunshine et al. |
| 2018/0195218 | A1 | 7/2018 | Hamada et al. |
| 2018/0195985 | A1 | 7/2018 | Nebuya |
| 2018/0249767 | A1 | 9/2018 | Begriche et al. |
| 2018/0258562 | A1 | 9/2018 | Fukuhara |
| 2018/0279930 | A1 | 10/2018 | Coppede et al. |
| 2019/0003083 | A1 | 1/2019 | Carlsson et al. |
| 2019/0055678 | A1 | 2/2019 | Hightower et al. |
| 2019/0156972 | A1 | 5/2019 | Kondo et al. |
| 2019/0167192 | A1 | 6/2019 | Frouin et al. |
| 2019/0354242 | A1 | 11/2019 | Cobanoglu et al. |
| 2020/0123689 | A1 | 4/2020 | Zhang et al. |
| 2020/0199790 | A1 | 6/2020 | Hayashi |
| 2020/0270775 | A1 | 8/2020 | Oppenheim |
| 2020/0325603 | A1 | 10/2020 | King et al. |
| 2020/0345083 | A1 | 11/2020 | Threlkeld |
| 2020/0347527 | A1 | 11/2020 | Konukoglu et al. |
| 2021/0207294 | A1 | 7/2021 | Threlkeld |
| 2021/0277544 | A1 | 9/2021 | King et al. |

FOREIGN PATENT DOCUMENTS

| | | |
|---|---|---|
| EP | 532468 A1 | 3/1993 |
| EP | 1482079 B1 | 7/2007 |
| EP | 3090082 B1 | 11/2017 |
| FR | 3061851 A1 | 7/2018 |
| SK | 2082017 U1 | 4/2018 |
| WO | 2001/002052 A2 | 1/2001 |
| WO | 2004097089 A1 | 11/2004 |
| WO | WO2009013704 * | 1/2009 |
| WO | 2014/138204 A1 | 9/2014 |
| WO | 2014/165997 A1 | 10/2014 |
| WO | 2015/022671 A1 | 2/2015 |
| WO | 2017/095861 A1 | 6/2017 |
| WO | 2017/111687 A1 | 6/2017 |
| WO | 2018/020169 A1 | 2/2018 |
| WO | WO2018020169 * | 2/2018 |
| WO | 2018/128584 A1 | 7/2018 |
| WO | 2019/134031 A2 | 7/2019 |
| WO | 2019/143694 A1 | 7/2019 |
| WO | 2019/145891 A1 | 8/2019 |

OTHER PUBLICATIONS

U.S. Appl. No. 16/845,796, filed Apr. 10, 2020, Machine-Knittable Conductive Hybrid Yarns.
International Search Report and Written Opinion for International Application No. PCT/US2020/027697, dated Jul. 9, 2020 (14 pages).
International Search Report and Written Opinion for International Application No. PCT/US2020/027699, dated Jul. 9, 2020 (13 pages).

(56) References Cited

OTHER PUBLICATIONS

International Search Report and Written Opinion for International Application No. PCT/US2020/027695, dated Jul. 23, 2020 (13 pages).
Weder, et al. Embroidered Electrode with Silver/Titanium Coating for Long-Term ECG Monitoring. Sensors 15, pp. 1750-1759, 2015. Retrieved from the Internet under https://www.mdpl.com/1424-8220/15/1/1750 on Mar. 23, 2020.
International Preliminary Report on Patentability for International Application No. PCT/US2020/027695, dated Sep. 28, 2021 (11 pages).
International Preliminary Report on Patentability for International Application No. PCT/US2020/027697, dated Sep. 28, 2021 (8 pages).
International Preliminary Report on Patentability for International Application No. PCT/US2020/027699, dated Sep. 28, 2021 (11 pages).
Supplementary European Search Report for EP Application No. 20787834.9, PCT/US2020027695 dated May 22, 2023 (9 pages).
Lee et al. "Knit Band Sensor for Myoelectric Control of Surface EMG-Based Prosthetic Hand" IEEE Sensors Journal, vol. 18, No. 20, Oct. 15, 2018, pp. 8578-8586.
No Author Listed "Kevlar Aramid Fiber Technical Guide" Dupont. Retrieved from the internet on Jul. 6, 2022 under https://www.dupont.com/content/dam/dupont/amer/US/en/safety/public/documents/en/Kevlar_Technical_Guide_0319.pdf (24 pages).
No Author Listed "Twaron—a versitile high-performance fiber" Teijin Aramid. Retrieved from the internet on Jul. 6, 2022 under https://www.teijinaramid.com/wp-content/uploads/2016/07/Product-Brochure-Twaron.pdf (7 pages).
Norholt, M. (1989). The Structure and Properties of Aramid Fibres. In: Bunsell, A.R., Lamicq, P., Massiah, A. (eds) Developments in the Science and Technology of Composite Materials. Springer, Dordrecht, Chapter 44, 2 pages.
Supplementary European Search Report for EP Application No. 20786809.2 dated Nov. 21, 2022 (8 pages).
Supplementary European Search Report for EP Application No. 20787051.0 dated Apr. 25, 2023 (11 pages).

* cited by examiner

SYSTEMS FOR MAINTAINING MOISTURE IN A TEXTILE ELECTRODE

CROSS-REFERENCE TO RELATED APPLICATIONS

This application claims priority from U.S. Provisional Application Ser. No. 62/832,098 filed Apr. 10, 2019 and entitled GARMENTS WITH INTEGRATED ELECTRODES AND CONDUCTIVE TRACES; from U.S. Provisional Application Ser. No. 62/832,101 filed Apr. 10, 2019 and entitled SYSTEMS AND METHODS FOR MAINTAINING MOISTURE IN A TEXTILE ELECTRODE; and from U.S. Provisional Application Ser. No. 62/832,104 filed Apr. 10, 2019 and entitled HYBRID YARN FOR WEAVING CONDUCTIVE WIRES INTO FABRIC. The contents of U.S. Provisional Application Ser. No. 62/832,098, U.S. Provisional Application Ser. No. 62/832,104, and U.S. Provisional Application Ser. No. 62/832,101 are hereby incorporated in their entireties by reference.

The subject matter of this patent application may be related to the subject matter of U.S. patent application Ser. No. 16/845,772 entitled KNITTED TEXTILES WITH CONDUCTIVE TRACES OF A HYBRID YARN AND METHODS OF KNITTING THE SAME filed on Apr. 10, 2020, and U.S. patent application Ser. No. 16/845,796 entitled MACHINE-KNITTABLE CONDUCTIVE HYBRID YARNS, filed Apr. 10, 2020. Each of these patent applications is hereby incorporated herein by reference in its entirety.

GOVERNMENT RIGHTS

This invention was made with Government support under Grant No. N00189-17-C-Z023 awarded by the U.S. Navy. The Government has certain rights in the invention.

FIELD

This disclosure relates to a passive system for retaining moisture in a textile electrode worn against the skin.

BACKGROUND

It is known to use textile electrodes for measuring physiological parameters of the human body. The use of textile electrodes, however, is constrained by their high impedance when their conducting material is dry. In addition, electrodes constructed from conductive threads woven or knitted together and placed against bare skin obtain relatively poor physiological signal quality (e.g., an electrocardiographic signal which is representative of the heart activity of a user) as compared to traditional electrodes which often use a highly conductive fluid or gel to place the electrode or conductive element in electrical contact with the user's skin. The gel or fluid reduces the impedance in contact with the electrode so that very small changes of electrical signals such as those measured by electroencephalography (EEG), electrocardiography (ECG) and electromyography (EMG) can be measured.

Prior art textile electrodes known by the inventors have attempted to improve their signal quality by ensuring the presence of moisture between the electrodes and the skin to allow ionic conduction between the two interfaces and thus, obtain a sufficient conductivity to detect signals generated by the human body. Typical system either provide a source of fluid to the electrode that maintains a moisture level between the electrode and the user's skin or rely on sweat generated by the user using physical activity to maintain a moisture level. The latter approach is highly dependent on the user's sweat output and level of physical activity, and severely limits the usefulness of the textile electrode. The former has to contend with the high level of fluid evaporation and absorption that can make the performance of the electrode unpredictable as the moisture level fluctuates depending on the user activity and environment.

In response, the prior art has taken one of two common approaches to maintain the moisture level in a textile electrode. The first adds a separate fluid reservoir and a system for moving fluid from the reservoir to the electrode. The second places a wetted material behind the electrode and separates the two by a semi-permeable membrane that allows moisture to flow from the wetted material to the electrode.

Both approaches, however, have serious drawbacks. Reservoir systems, for example, add a bulky fluid container that must be placed somewhere on the user, and can require an active transport mechanism in order to move fluid to the electrode. Systems with semi-permeable barriers are difficult to rewet, dry, and clean, which makes their wetted material prone to bacteria growth and breakdown.

SUMMARY

The present disclosure relates to a system for continuously humidifying a textile electrode during its use by a human being. Certain embodiments of the present disclosure provide for a system for maintaining a moisture content of a textile electrode, where the textile electrode is part of a garment and the textile electrode is positioned against the skin of a wearing of the garment. Some embodiments include a reservoir made from a material with hydrophilic and hydrophobic properties. In some instances, the reservoir is made from a skincore material such as natural wool, which has a hydrophilic or hygroscopic cortex and a hydrophobic exterior, positioned directly against the side of a textile electrode opposite the user's skin. Some embodiments also include an impermeable outer sealing layer surrounding the skincore material and the textile electrode, such that the outer sealing layer extends beyond the outer edges of the textile electrode. The impermeable material is heat activated at the outer edge such that the material flows into the textile beyond the edges of the textile electrode and forms a moisture barrier surrounding the edges of the textile electrode. Some embodiments also include an electrical contact point on the textile electrode that is connecting one or more conductive wires from outside the sealing layer to the textile electrode. In some instances, an inner sealing layer is disposed around the electrical contact to separate the conductive wires and the portion of the textile electrode in contact with the conductive wires from moisture of the skincore material and the user's skin. The skincore material inside the sealing layer is configured to receive and retain moisture from the user's skin through the textile electrode, as well as from a pre-wetting application of a fluid, such as water or saltwater, to the exposed user-facing side of the textile electrode.

In operation, some embodiments of the present system control the humidity or moisture level present in a textile electrode by providing a reservoir material directly against the electrode that, due to the material properties of the reservoir material, is able to maintain a high level of moisture in the textile electrode while the textile electrode and outer sealing layer is positioned against the user's skin.

The initial wetting of the reservoir material can, in some instances, provide enough moisture to allow the textile electrode to function at a desired level for many hours, depending on the size and amount of fluid initially added to the reservoir material. The hydrophobic properties of the exterior of the reservoir material prevent excess evaporation due to exposed fluid, and the hydrophilic properties of the interior of the reservoir material allow substantial fluid retention and controlled evaporation of that fluid to the textile electrode over a long period of time. Additionally, the hydrophilic properties of the reservoir material enable the reservoir to readily absorb moisture from sweat excreted from the user's skin adjacent to the textile electrode. The outer sealing layer's contact with the user's skin surrounding the textile electrode helps to retain this excreted moisture inside the outer sealing layer where it can humidify the textile electrode and excess moisture can be stored by the reservoir material for later evaporation when the textile electrode's moisture level drops below that of the reservoir material.

In operation, by controlling the humidity level of the textile electrode, some embodiments of the present disclosure provide a system for maintaining optimum electrical signals reception by the textile electrode while allowing to be worn for long periods; thereby achieving quality measurements. Some embodiments of the present disclosure also provide for a system designed to operate in the normal life cycle of a garment, including reuse and multiple washes. Because the textile electrode and reservoir material are exposed to the interior side (i.e., user-facing side) of the garment, washing and cleaning of the reservoir material is not inhibited by the outer sealing layer, which is the same mechanism by which the reservoir material can be pre-wetted before use by simply applying a fluid to the inner side of the textile electrode.

Some embodiments of the present disclosure provide for a system designed to be simple to incorporate into a garment and operate in the normal life cycle of a measure of the person wearing the garment. During this cycle, the body contact provides for retention of moisture in the reservoir material, as well as a resupply of moisture from the user's sweat. Additionally, heat from the user's skin helps to heat the reservoir material, which helps release moisture from the reservoir material. Thus, some embodiments of the present disclosure provide for a passive system for maintaining the moisture content of a textile electrode during use of the garment. Additionally, some embodiments of the present disclosure provide for a system that can be integrated into a garment with little to no noticeable change in the garment's feel or function beyond the present of moisture in the regions of the garment with textile electrodes. Some embodiments of the present disclosure provide for flexible materials that can be integrated into a garment to so as to not inhibit contact between the inner side of the textile electrode and the user's skin, which improves the quality and reliability of the electrical signal received by the textile electrode.

Certain embodiments of the present disclosure include a system for maintaining moisture in a textile electrode. The system can include a textile layer having a textile electrode region knitted therein and an insulated region adjacent to the textile electrode region, a reservoir material positioned above the outer side of the textile electrode region, and an outer sealing layer positioned above the reservoir material, the outer sealing layer extending over and around the reservoir material and the textile electrode region. The textile electrode region and insulated region together can define a continuous textile section. The textile layer can have an inner side and an outer side opposite the inner side, the inner side of the textile electrode region being exposed and configured to contact against a user's skin. The textile electrode region can be knitted from an electrically conductive yarn having an exposed electrically conductive surface and the insulated region can be knitted from an electrically insulated or electrically inert yarn. The outer sealing layer can extend through a thickness of the textile layer to the inner side of the textile layer. In some embodiments, the outer sealing layer defines a moistures barrier around the textile electrode region and the reservoir material and through the thickness of the textile layer around the textile electrode.

The system can include an electrical contact between a conductive wire received through the outer sealing layer and the textile electrode. In some embodiments, the system includes an inner sealing layer surrounding the electrical contact.

The exposed electrically conductive surface of the electrically conductive yarn can include a silver coating. The outer sealing layer can include an exterior film layer above the reservoir material and the textile electrode region and an adhesive material securing the exterior film to the textile layer, with the adhesive material extending through the thickness of the textile layer to the inner side of the textile layer.

In some embodiments, the insulated region includes a conductive trace region knitted therein, the conductive trace region extending from a border of the textile electrode and through the outer sealing layer. The conductive trace region can be knitted from a hybrid yarn containing a non-conductive yarn twisted with a conductive wire, the conductive wire having an exterior coating with an insulating material, and the textile electrode region can be electrically connected to a conductive wire from the conductive trace region that the exterior coating removed. In some embodiments, the insulated region includes an electrical inert region, with the conductive trace region extending through the electrically inert region and the electrical inert region is knitted from an electrically inert yarn. The textile layer having the textile electrode can be a first layer, with the system further includes a second layer of the hybrid yarn knitted out of the conductive trace region and over a portion of the electrode region to form a two-layer section in the textile electrode region, where the exterior coating of the conductive wire of a portion of the conductive trace region in the two layer section is removed to expose a portion of the conductive wire and the exposed portion of the conductive wire is electrically connected with the electrode region via a conductive material. In some embodiments, the non-conductive yarn is removed where the exposed portion of the conductive wire is electrically connected with the electrode region and an inner sealing layer can surround the exposed portion of the conductive wire.

The reservoir material can include a skincore fiber having a hydrophilic or hygroscopic cortex and a hydrophobic exterior. The reservoir material can be natural wool and can be felted. The textile layer can include a single knitted layer, which can be knitting using intarsia knitting. In some embodiments, the textile layer defines a garment. In some embodiments, the electrode region is configured to pick up electrical signals from the user's body. In some embodiments, the insulated region surrounds the textile electrode region.

Other implementations, features, and advantages of the subject matter included herein will be apparent from the description and drawings, and from the claims.

BRIEF DESCRIPTION OF THE DRAWINGS

This disclosure will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Example Textiles with Integrated Conductive Traces

Figure 1A:
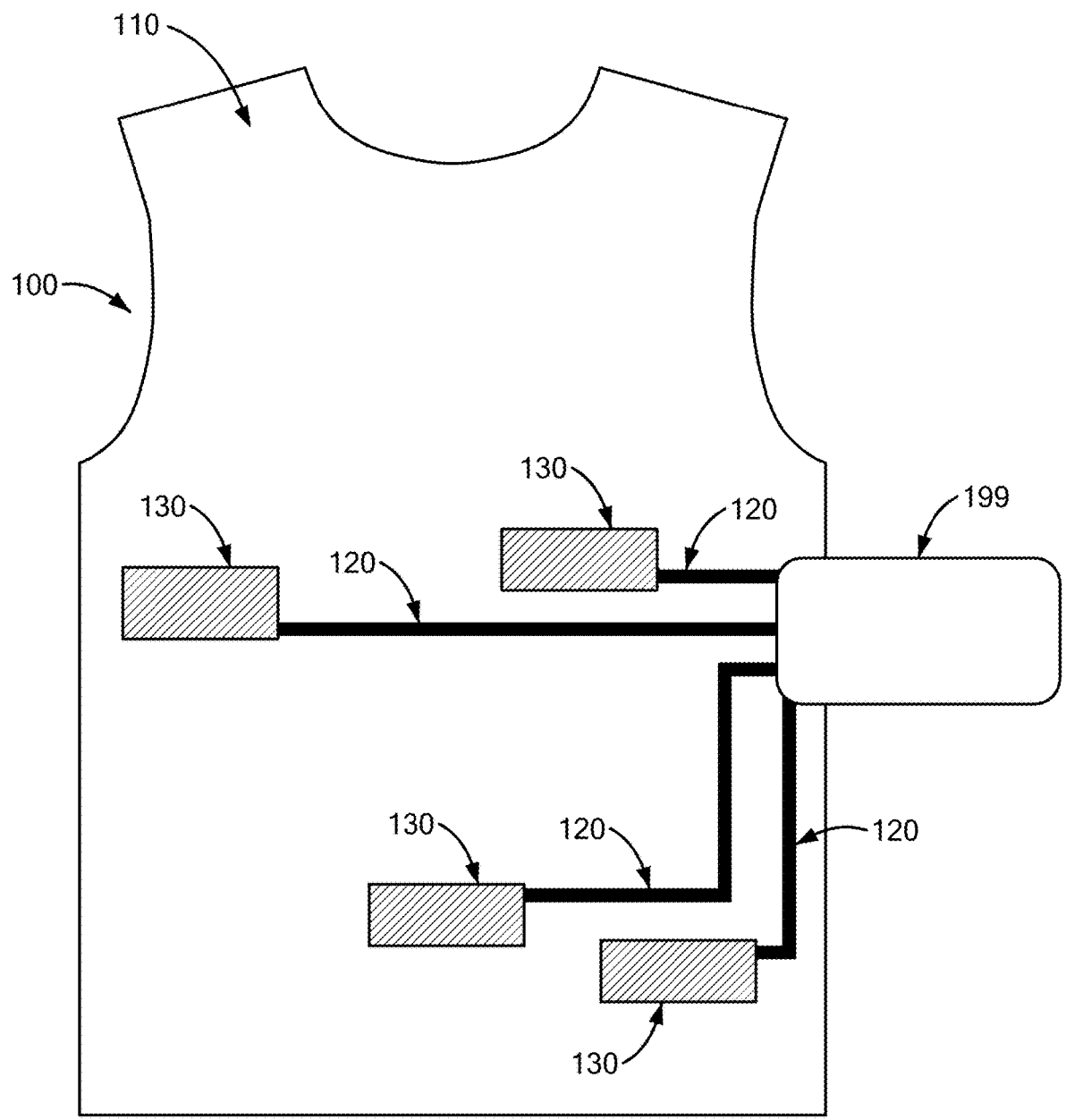
FIG. 1A is a schematic illustration of a single-layer textile formed as a wearable garment with integrated textile electrodes and conductive traces connecting the electrodes to a controller unit configured in accordance with illustrative embodiments.

FIG. 1A is a schematic illustration of a textile formed as a wearable garment with integrated electrodes and conductive traces connecting the electrodes to a controller unit configured in accordance with illustrative embodiments. Specifically, FIG. 1A schematically shows a textile garment 100 with integrated textile electrodes 130, and conductive traces 120 connecting the textile electrodes 130 to an electrical device 199. The garment 100 is constructed as a single textile layer to be worn directly against the skin. The garment 100 is knitted from a regular electrically inert material 110 (e.g., an insulator material, such as cotton, wool, or polyester) with the textile electrodes 130 knitted directly into the garment 100, without adding additional textile layers at the location of the textile electrodes 130. The conductive traces 120 are knitted with a hybrid yarn, discussed in more detail below, that is constructed from a strong and inelastic nonconductive yarn twisted with one or more conductive wires, with the conductive wires being coated with an insulating material. The hybrid yarn enables the conductive traces 120 to transmit power or electrical signals through the conductive wires without interference due to the insulating coating on the conductive wires. The textile electrodes 130 have an inner surface that is therefore positioned against the user's skin when the garment 100 is worn. The textile electrodes 130 are knitted from a conductive yarn, such as a silver coated polyester, that enables the textile electrodes 130 to conduct electrical signals across the textile electrode 130. The textile electrodes 130 are connected to the electrical device 199 via conductive traces 120 that are also knitted directly into the garment 100 without adding additional layers to the garment. In some embodiments, the garment 100 defines a single-layer knitted textile layer across the inert material 110, the textile electrodes 130, and the conductive traces 120. In some embodiments, the textile electrodes 130 are knitted as electrical connection regions for a sensor or electronic device affixed to the garment 100.

The textile electrodes 130 can be arranged to, for example, pick up or sense electrical signals from the user's body, such as those related to heart rate and heart function (e.g., the signals for use in forming an electrocardiogram EKG). In some embodiments, the garment 100 includes four textile electrodes 130, positioned with respect to the user's body in order to provide a high-quality EKG signal. The conductive traces 120 connect the textile electrodes 130 to the electrical device 199 via the conductive wires integrated into the hybrid yarn from which the conductive traces 120 are knitted. The conductive wire of the hybrid yarn can be coated with an insulating polymer, which is able to be removed at the points of contact with the textile electrodes 130 and the electrical device 199.

In some embodiments, the hybrid yarn is constructed from a highly inelastic material, such as meta-aramid or para-aramid (e.g., Kevlar® or Twaron®) or a material with similar material properties to protect the integrated conductive wires from damage or being severed during the knitting process and being damaged or severed during normal wear of the garment 100, such as Ultra High Molecular Weight Polyethene (UHMWPE), Polybenzimidazole (PBI), Polyphenylene Benzobisoxazole (PBO), High Strength Polyester, Liquid-Crystal Polymer (LCP), or spider silk. In some embodiments the hybrid yarn is made with a fire retardant and self-extinguishing material, such as para-aramid or material with similar properties according to the ASTM D6413/D6413M Standard Vertical Test Method for Flame Resistance of Textiles to enable the insulating layer and nonconductive yarn to be removed using ablation. The conductive wire can be, for example copper wire or copper-clad stainless-steel sire. Additionally, the textile electrodes 130 may be knitted or otherwise constructed with a conductive wire, such as silver or copper wire or a nonconductive yarn (e.g., nylon, polyester, cotton, or wool) coated with a conductive material such as silver or copper. In some embodiments, the standard material 110, textile electrodes 130, and conductive traces 120 are knitted together into a single-layer garment 100 without seams.

Figure 1B:
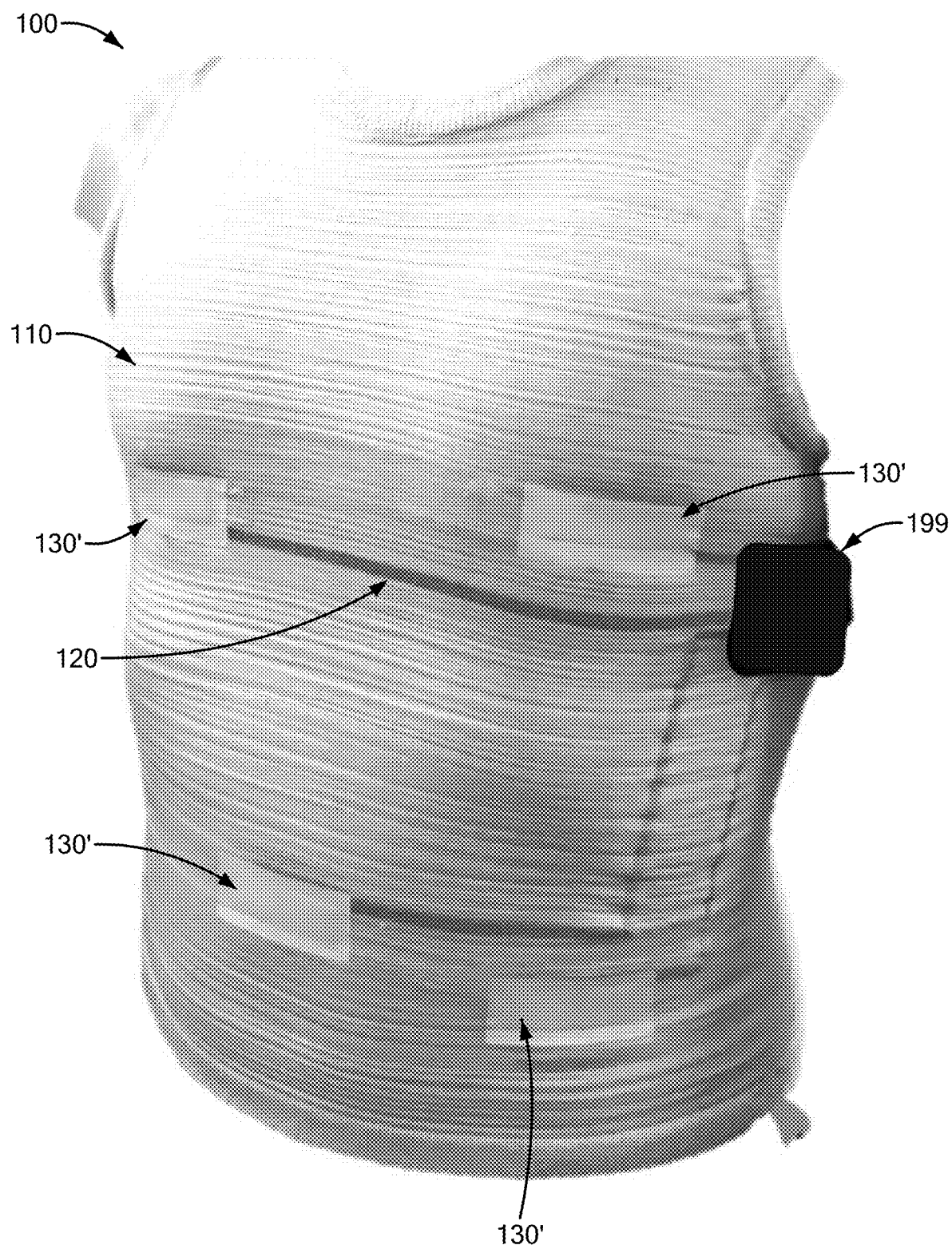
FIG. 1B is a photograph of an illustrative embodiment of the textile of FIG. 1A on a user.

FIG. 1B is a photograph of an illustrative embodiment of the textile of garment 100 FIG. 1A on a user. FIG. 1B shows patches 130' over the textile electrodes 130 that are arranged to maintain a moisture level in the textile electrode 130. These patches 130' can also be used to impart stability to the textile electrode on body when the garment is worn and to reduce electrical static noise from the outer surface of the textile electrode 130.

Example of a Hybrid Conductive Yarn

Figure 2A:
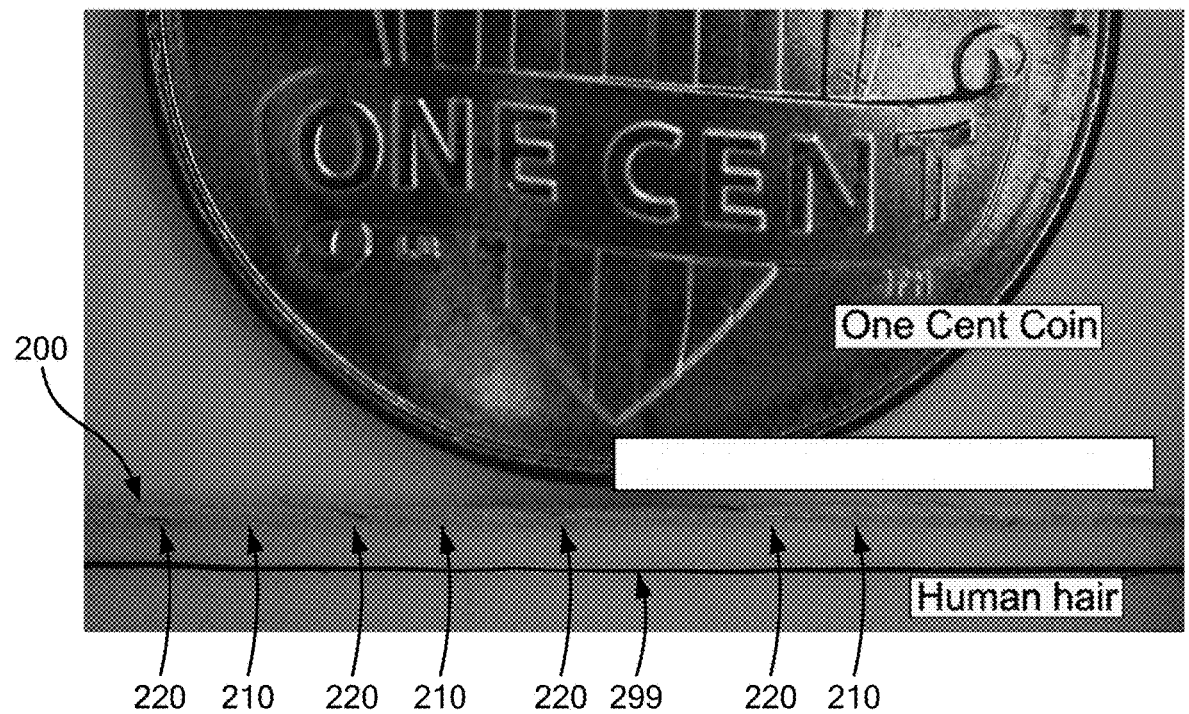
FIG. 2A is a photograph of an illustrative embodiments of a hybrid yarn.

FIG. 2A is a photograph of a strand of a hybrid yarn 200 configured in accordance with illustrative embodiments. To show its relative size, the hybrid yarn 200 is compared with a U.S. penny and a strand of human hair 299. Preferably, the hybrid yarn 200 is made from a nonconductive yarn 210 and a conductive wire 220 twisted together. In some instances, the nonconductive yarn 210 has minimal elasticity and high strength, and is made from, for example, a meta-aramid or para-aramid material. The nonconductive yarn 210 also can be made from filament or staple fibers. The conductive wire 220 can be insulated with, for example, a polyurethane coating. In some instances, the hybrid yarn 200 can be bonded with a coating (e.g., Nylon) for softer feel and maintain the integrity of the hybrid yarn 200.

In one example, the hybrid yarn 200 includes two stands of copper-clad stainless steel or copper with between 5 to 12 twists per inch around a Kevlar strand. The 5 to 12 twists per inch construction is for a strand of Kevlar and a 50 micron conductive wire (e.g., 43 micron thick metal and a 3-4 micron thick coating of polyurethane) that when twisted together suitable to knit a textile at 15 gauge. The hybrid yarn in FIG. 2 is made from two copper clad stainless-steel wires 220 twisted with a Kevlar yarn 122 at 9 twists per inch. In some instances, other nonconductive yarns 210 can be used, such as Vectran® or Twaron®, which are also a high strength yarns with low elasticity.

Nonconductive yarns 210 made with para aramid or similar materials have many advantages, such as being strong, but relatively light. The specific tensile strength (stretching or pulling strength) of both Kevlar 29 and Kevlar 49 is over eight times greater than that of steel wire. Unlike most plastics it does not melt: it is reasonably good at withstanding temperatures and decomposes only at about 450° C. (850° F.).

Accordingly, the hybrid yarn 200 can be laser ablated or burned to remove the nonconductive yarn 210 and the coating on the conductive wire 220.

Figure 2B:
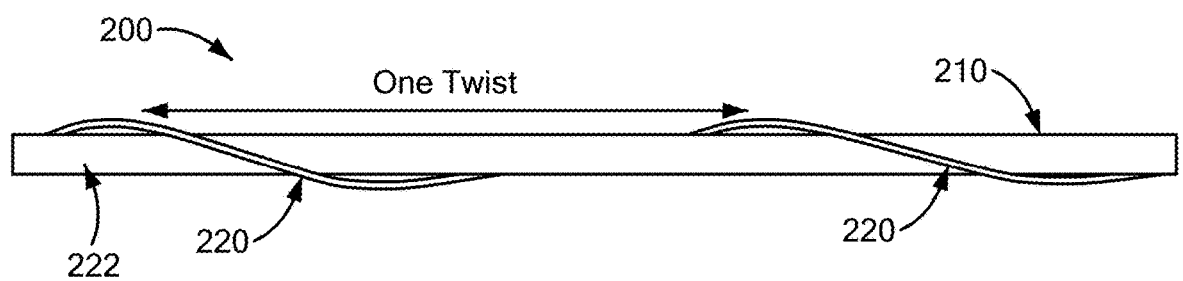
FIG. 2B is a schematic illustration example twist patterns of a conductive wire around a nonconductive yarn.

FIG. 2B is a schematic illustration of an example twist pattern of a hybrid yarn 200 having a conductive wire 220 around a nonconductive yarn 210. In order to knit the conductive traces 120 into a single-layer using a flatbed knitting machine the nonconductive yarn 210 must protect conductive wire 220 from being broken by the stresses put on the hybrid yarn 200 by the flatbed knitting machine. According, a hybrid yarn 200 was developed that was suitable for flatbed knitting. The hybrid yarn 200 is constructed from the nonconductive yarn 210 being twisted with the conductive wire 220, where the nonconductive yarn 210 is a strong and inelastic yarn that, when exposed to the tensile forces of the flatbed knitting machine, exhibits an elongation of a sufficiently small percentage to prevent breakage of the conductive wire 220. For example, the nonconductive yarn 210 may have a tensile strength greater than that of the conductive wire 220 as well as an elongation break percentage less than 5 or less than about 4.2. In other embodiments, the nonconductive yarn 210 may have a Young's modulus of 60 or greater. In practice, because the nonconductive yarn 210 and conductive wire 220 are twisted together and the nonconductive yarn 210 comprises the majority fraction of the overall cross-section of the hybrid yarn 200, the material of nonconductive yarn 210 need not simply be less elastic than the metal of conductive wire 220 because, as the hybrid yarn 200 is exposed to tensile forces, the hybrid yarn 200 acts as a single structure and the relative elasticity of the much larger nonconductive yarn 210 section is less than the relative elasticity of the much thinner conductive wire 220 as the hybrid yarn 200 undergoes tension. Accordingly, suitable embodiments of hybrid yarn 200 are constructed from very strong and inelastic fibers, such as meta-aramids and para-aramids, that are both thin and flexible enough to be knitted on a flatbed machine, but also strong and inelastic enough at those thin diameters to be twisted with a substantially thinner metal wire (e.g., a conductive wire 220 thin enough to maintain the thin and flexible properties of the overall hybrid yarn 200 that enable it to be both machine knittable and not affect the worn feeling of a garment) and prevent the substantially thinner metal wire from breaking.

Examples of Connecting a Hybrid Conductive Yarn to a Textile Electrode

Figure 3:
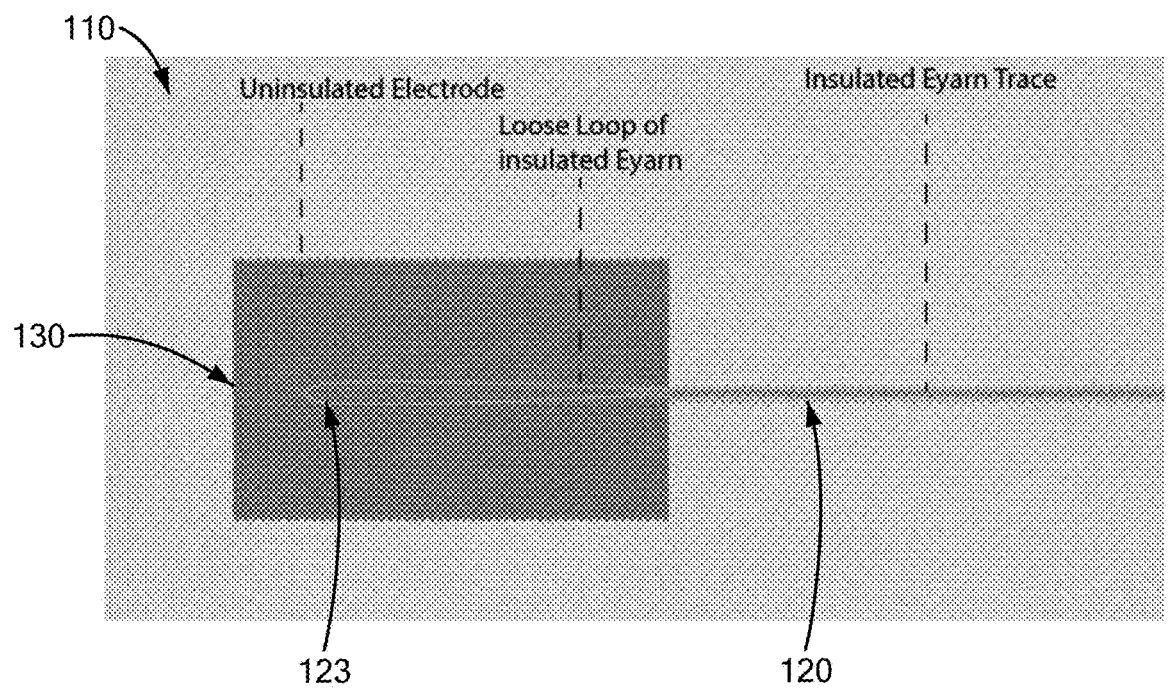
FIG. 3 is a photograph of an embodiment of a knitted textile having a textile electrode and a conductive trace region with a loose loop of hybrid yarn from the conductive trace extending across the textile electrode.

FIG. 3 is a photograph of an embodiment of a knitted textile having an integrated electrode region 130 and a conductive trace region 120 with a loose loop 123 of hybrid yarn 200 from the conductive trace region 120 extending across the face of the textile electrode region. The loop 123 can be cut into a tail in order to facilitate connection between the textile electrode region 130 and the conductive trace region 120 of which the loop or tail is an extension of the same hybrid yarn 200. The loose loop 123 can be used to electrically connect the conductive trace region 120 to the textile electrode region 130 by removing the insulating layer (and, in some embodiments, the nonconductive yarn) from the loop 123 and connecting the now-bare conductive wire 220 of the loop 123 to the conductive yarn of the textile electrode region 130. Leaving this loop 123 loose allows the loop 123 to be ablated, exposing the bare conductive wire 220, without destroying the textile 100, 120, 130. In some embodiments, the loose loop 123 increases the surface area of the conductive wire 220 that is able to be connected to the electrode, as well as providing a free strand to more easily remove the insulating coating and nonconductive yarn.

Figure 4:
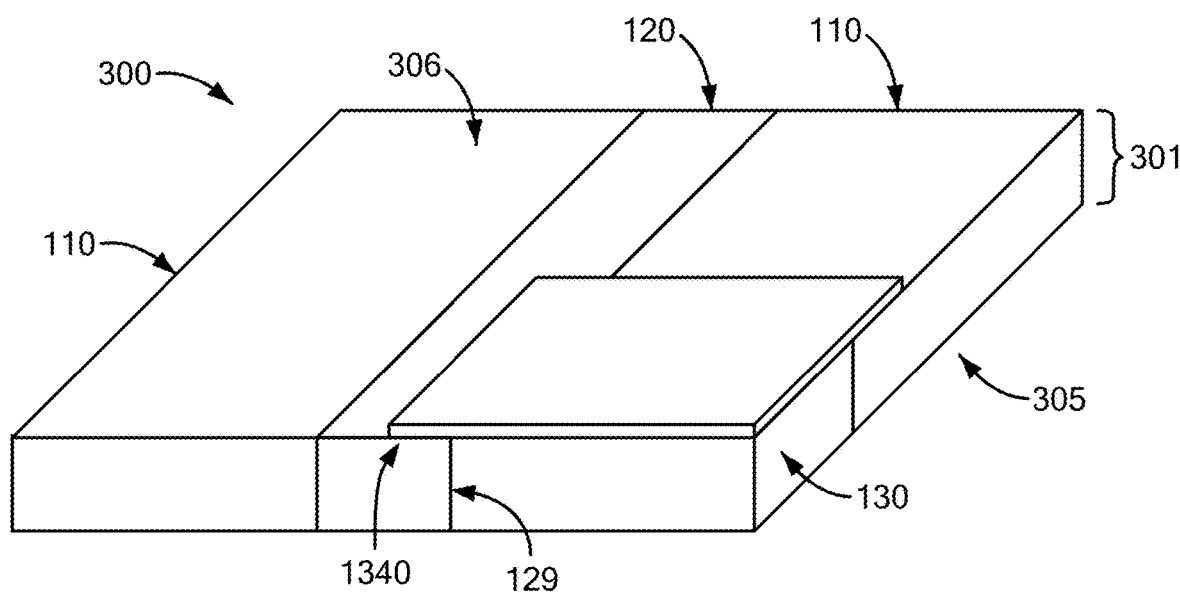
FIG. 4 is a schematic illustration of a single layer of a continuous textile section knitted having a conductive trace region passing through an inert region and electrically connected to an electrode region of the textile section.

FIG. 4 is a schematic illustration of a single-layer 301 of a continuous textile section 300 knitted to have a conductive trace region 120 passing through an inert region 110, with the conductive trace region 120 being electrically connected to a textile electrode region 130 of the textile section 300 at an interface 129 between the two regions. The single 301 defines a bottom side 305 and a top side 306 opposite the bottom side, with each region 110, 120, 130 extending between the top side 306 and the bottom side 305. Additionally, FIG. 4 shows a seal or patch 1340 positioned on the top side 306 of the textile electrode region 130.

Example Moisture Retaining Systems

Figure 5:
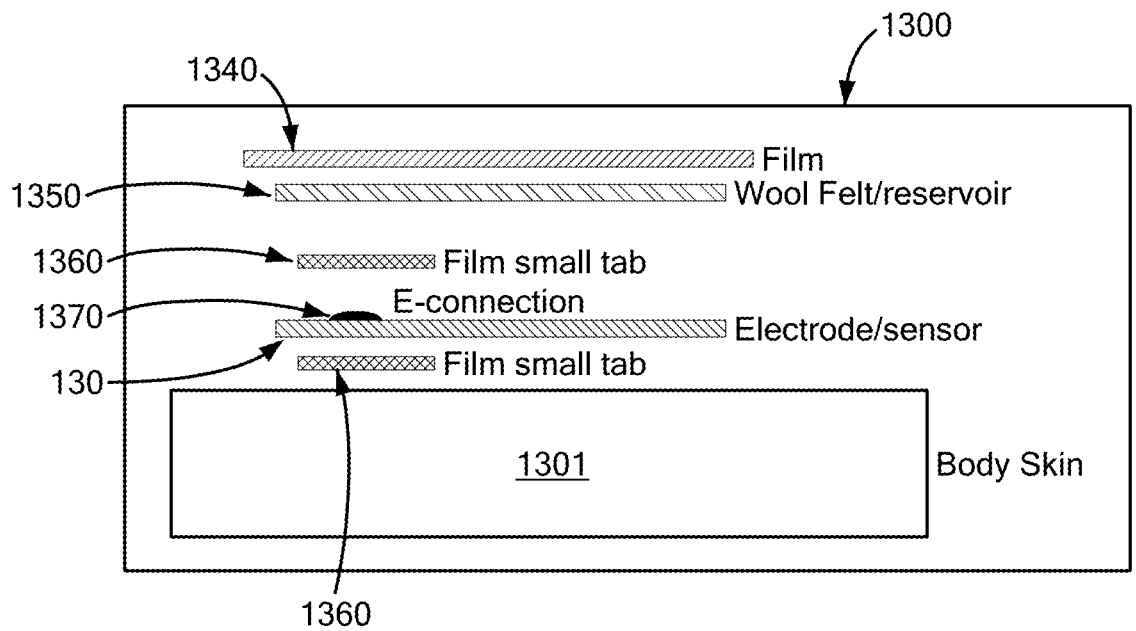
FIG. 5 is a schematic illustration of a reservoir system for maintaining moisture in a textile electrode in accordance with illustrative embodiments of the invention.

FIG. 5 is a schematic of a reservoir system for maintaining moisture in a textile electrode. The electrodes/sensors preferably are stabilized for electrical reasons. Among other benefits, stabilization of the electrode reduces noise, thus providing better data from the textile electrode region 130. Adding an outer film layer overcomes a constraint of a data gathering textile electrode-keeping it damp.

Specifically, data is more effectively captured when the textile electrode is stable and damp. As such, illustrative embodiments add an outer film layer around the textile electrode region 130.

For example, the added layer may include a thermoplastic adhesive cover film (or thermoplastic textile laminate) that mitigates evaporation of moisture from the region of the textile electrode region 130 through the garment 100. Moreover, adding an additional layer of fabric, between the textile electrode region 130 and the film improves sweat absorption. Multiple tests were conducted with a variety of different materials used as the hydrophilic layer, such as nonwoven wool batting, dense polyester knit (brand name Axe suede) and superhydrophobic fiber and superhydrophobic yarn (as produced by Technical Absorbents, Grimsby, UK). Framis 'Portofino' laminate (polyester jersey +TPU adhesive) and Framis 'Heavy Dream' (TPU Cover-Film) was used as a stabilization 'patch'. Here it was discovered that hydrophobic/hydrophilic materials, such as natural wool, are superior when used as the reservoir material. Natural wool absorbs salt water well and does not readily evaporate. Natural wool is also naturally fire resistant and has antimicrobial properties that are consistent with its intended use in this embodiment next to the skin. Further, natural wool washes and dries without deterioration. Other hydrophobic materials, such as those tested, can also be used to form the reservoir but wool has the best characteristics for performance in the garment 100. The wool can be any form including loose fiber, or layers of knitted or woven wool, or felted wool, or non-woven wool batting. While some embodiments are 100% wool, wool blended with other fibers at no less than 70% wool/30% other fibers can also be used.

FIG. 5 shows a cross-section of a textile electrode region 130 of a garment positioned in-use, against a user's base skin 1301, with a reservoir system 1300 for retaining moisture in the textile electrode region 130. The reservoir system includes an outer film layer 1340 above a reservoir material 1350, which is itself directly above the textile electrode region 130. The electrode can include an electrical contact 1370 that is separately sealed by an inner film 1360 from the rest of the textile electrode region 130, reservoir material 1350, and the user's skin 1301.

Figure 6:
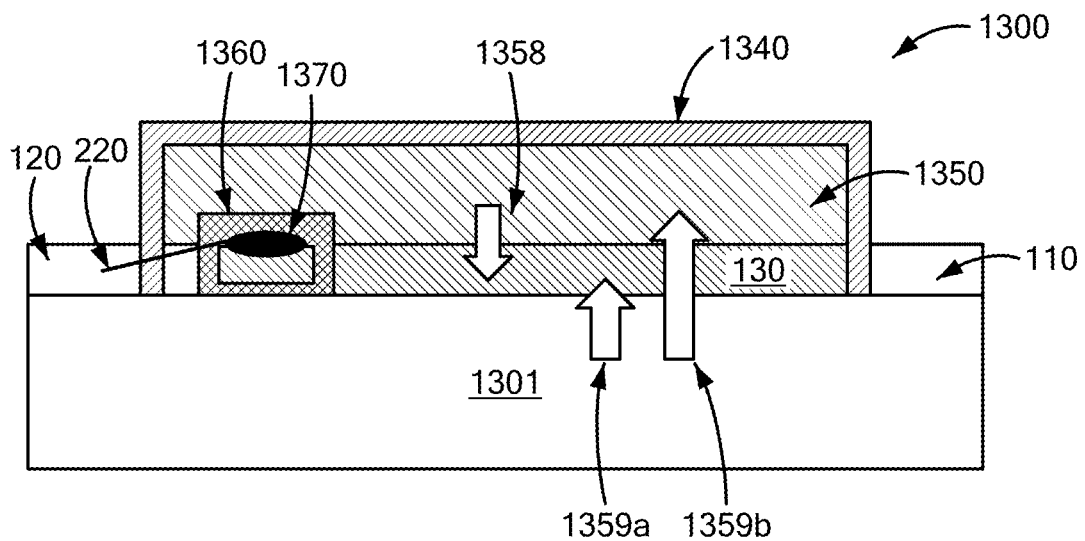
FIG. 6 is schematic illustration of a reservoir system for maintaining moisture in a textile electrode showing the connection between the textile electrode and a conductive wire of a hybrid yarn in accordance with various embodiments.
Figure 7:
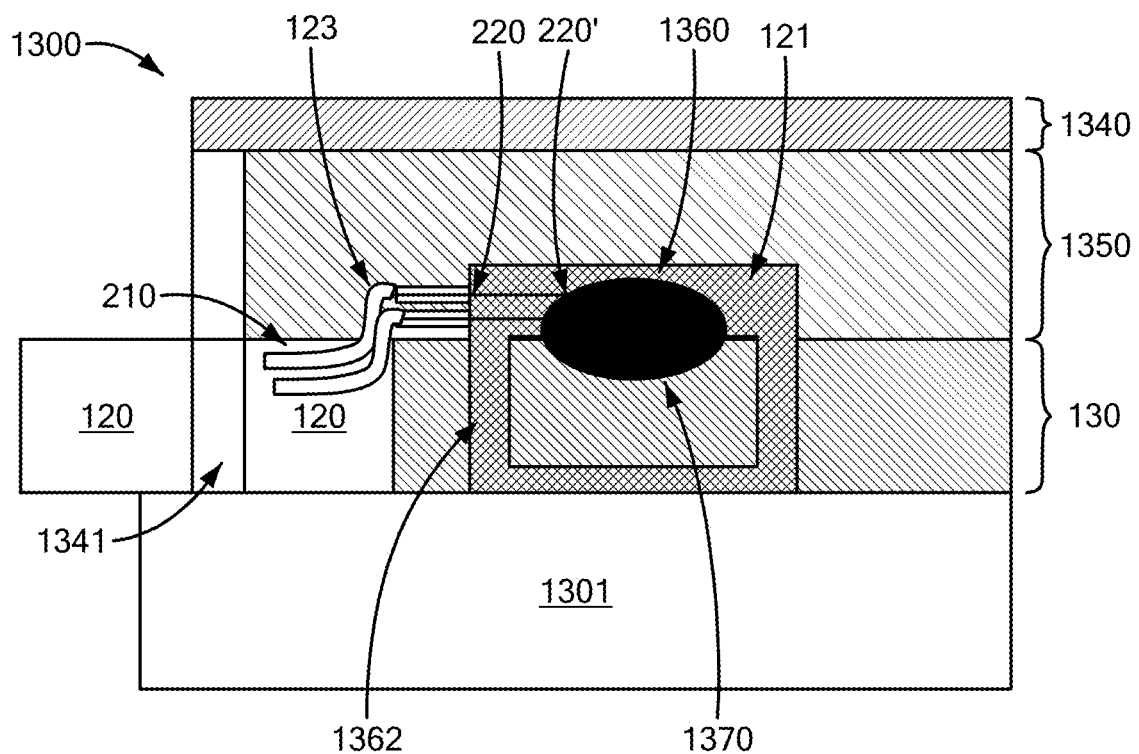
FIG. 7 is a schematic illustration of a reservoir system of FIG. 6 showing the connection between the textile electrode and the conductive wire in more detail.

FIGS. 6 and 7 are schematic drawings of the reservoir system 1300, which maintains moisture in a textile electrode region 130. These figures also show the connection between the textile electrode region 130 and a conductive wire 220 of a conducive trace 120 made from a hybrid yarn 1020. FIG. 6 shows the outer film layer 1340, surrounding the reservoir material 1350 and the textile electrode region 130, extending through the garment 100 (shown here as through the standard material 110 on one side and the conductive trace 120 on the other) to the inner side of the garment abutted against the user's skin 1301. In this manner, the outer layer 1340 encapsulates the textile electrode region 130 and the reservoir material 1350 with a water-proof barrier against the user's skin 1301. Inside the outer layer 1340, the water vapor from the reservoir material 1350 can flow into the textile electrode region 130 (shown as arrow 1358), and water vapor from the user's skin is able to flow into the electrode (shown as arrow 1359a) and into the reservoir material 1350 (shown as arrow 1359b). FIG. 6 also shows that a conductive wire 220 from the conductive trace 120 extends though the outer film 1340 and is connected to the conductive material of the textile electrode region 130 with an electrical connection 1370. In some instances, and as shown, the electrical connection 1370 is encapsulated by an inner film 1360 that prevents moisture from the textile electrode region 130, reservoir material 1350, or the user's skin 1301 from reaching the electrical connection 1370.

FIG. 7 is a detail view of the connection between the conductive trace 120 and the textile electrode region 130. FIG. 7 shows that a loop 123 of hybrid yarn, including a coated conductive wire 220 and a nonconductive yarn 210 extending from the conductive trace 120, though the outer film 1340. FIG. 7 also shows uncoated portion 220' of the conductive wire 220 extending through the inner film 1360 to the electrical connection 1370. In FIG. 7, a portion 1362 of the inner film 1360 can extend through the textile electrode region 130 in order to completely seal the electrical contact 1370 from moisture while still allowing the conductive material of the textile electrode region 130 to pass though the portion 1362 to maintain the electrical connection between the electrical contact 1370 and the rest of the textile electrode region 130.

Figure 8:
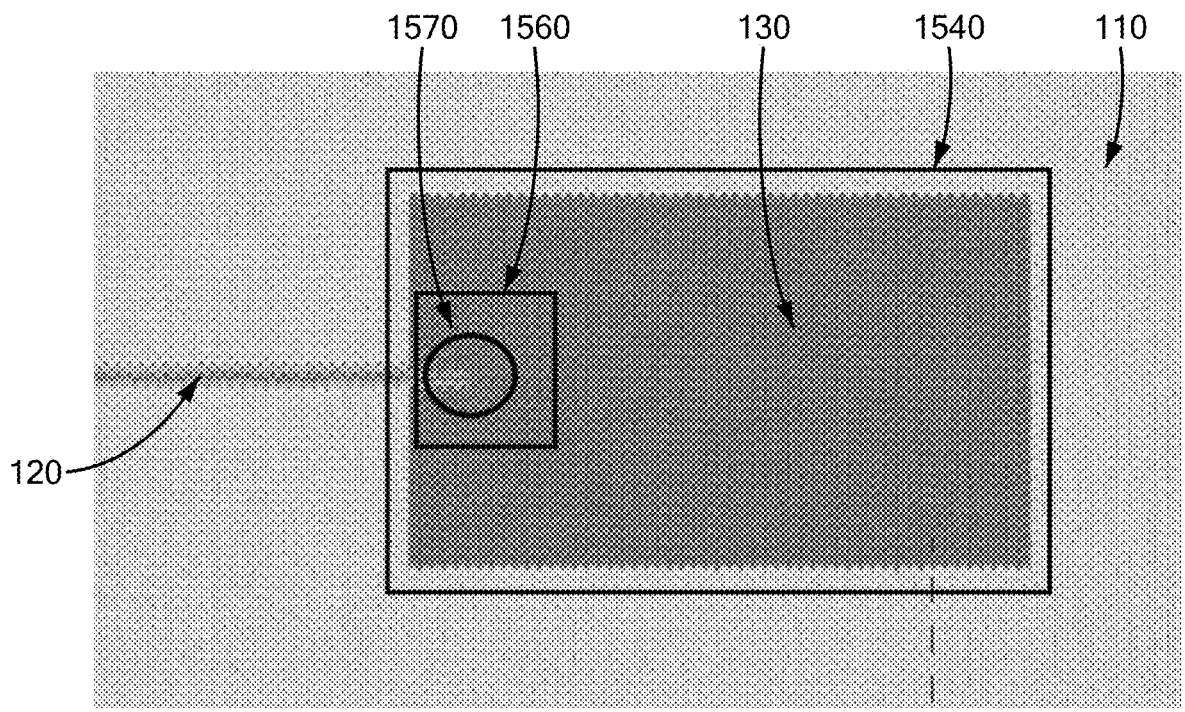
FIG. 8 is a photograph of a knitted textile embodiment having a textile electrode and a conductive trace extending into the textile electrode, showing the location of an electrical connection and a film seal.

FIG. 8 is a graphic rendering of a knitted textile embodiment having a textile electrode and a conductive trace extending into the textile electrode, showing the location of an electrical connect and a film seal. In FIG. 8, a section of the knitted textile garment 100 has an integrated textile electrode region 130 and a conductive trace 120 extending into the region of the integrated textile electrode region 130 after the knitting steps are completed. In operation, once the textile, including the conductive trace 120 and integrated textile electrode region 130 is knitted, the conductive wires 220 of the conductive trace 120 can be connected to the conductive material of the electrode by, for example, an ablation process, whereby a small section of the textile where the conductive trace 120 meets the textile electrode region 130 is ablated away, leaving only the uncoated conductive wires 220' behind. With the uncoated conductive wires 220' exposed, an electrical contact 1370 (e.g., a conductive material) can be added at the location of the exposed wires 220' to electrical connect the exposed wires 220' to the surrounding conductive material of the textile electrode region 130.

FIG. 8 shows the location of this electrical contact 1370 as a boxed region 1570. With the electrical contact 1370 created, an inner sealing layer or film 1360 can be placed around the electrical contact 1370 and though the surrounding textile 120, 130 such that the material of the inner film 1360 becomes integrated into the fibers of the surrounding textile 120, 130 to form a sealed moisture barrier around the electrical contact 1370, without interrupting the fibers of the textile electrode region 130, such that the electrical contact 1370 remains in electrical contact with the textile electrode region 130. With the inner sealing layer 1360 in player, the reservoir material 1350 can be placed above the electrode, and the outer sealing layer 1340 can seal the reservoir material 1350 and the textile electrode region 130 such that only the inner surface of the electrode (i.e., the skin-facing surface) is exposed inside a perimeter of the sealing layer 1340 extending into the fibers of textile around the textile electrode region 130, such that the moisture retained by the reservoir 1350 cannot escape through the garment. FIG. 8 indicates the location 1570 where the electrical connect 1370 can be placed, the location 1560 where the inner layer 1360 can be placed, and a location 1540 where an outer layer 1340 can be integrated with the material of the garment to surround the textile electrode region 130 and reservoir material 1350 after the reservoir material 1350 is placed on the textile electrode region 130.

Figure 9:
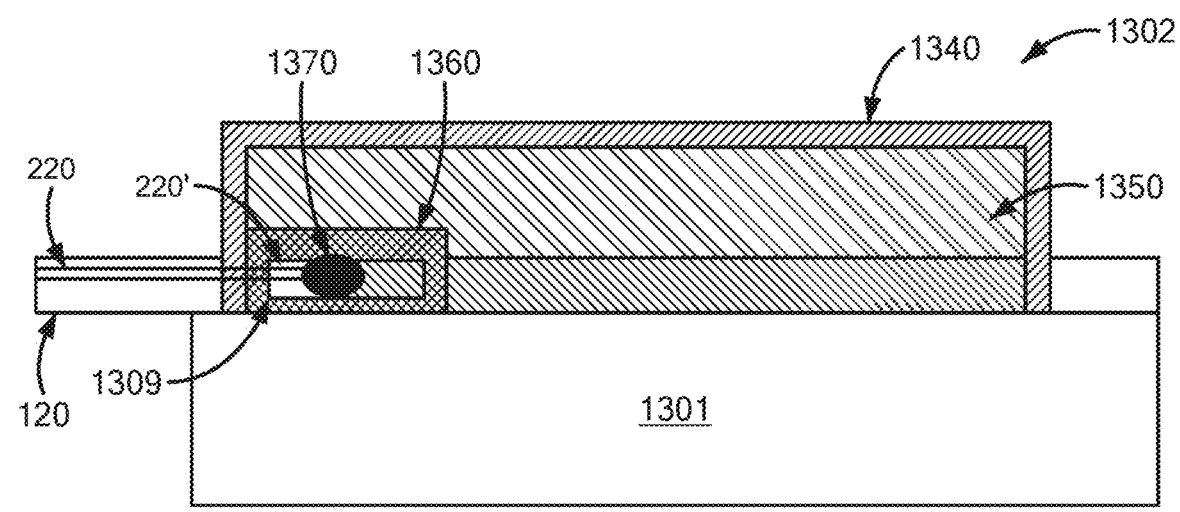
FIG. 9 is a schematic drawing of one embodiment of a reservoir system for maintaining moisture in a textile electrode showing the connection between the textile electrode and a conductive wire of a hybrid yarn.

FIG. 9 is a schematic drawing of one embodiment of a reservoir system for maintaining moisture in a textile electrode showing the connection between the textile electrode and a conductive wire of a hybrid yarn. In FIG. 9, a schematic of an alternate configuration of the reservoir system 1302 for maintaining moisture in a textile electrode region 130 is shown. Among other things, FIG. 9 shows the connection between the textile electrode region 130 and a conductive wire 220 of a hybrid yarn 200 in a conductive trace 120 in the garment 100. The conductive trace 120 is connected to the textile electrode region 130 where the two knitted materials meet. For example, an ablated region 1309 of a loop of the conductive trace 120 exposes the uncoated conductive wire 220'. The ablated loop is then bundled up and attached to the structure of the knit textile electrode region 130. Here, an electrical contact 1370 can be placed to improve the connection between the uncoated wire 220' and the textile electrode region 130. In some instances, the electrical contact 1370 includes a conductive plate or a bead of conductive metal, such a solder or conductive adhesive or uninsulated conductive yarn.

Figure 10:
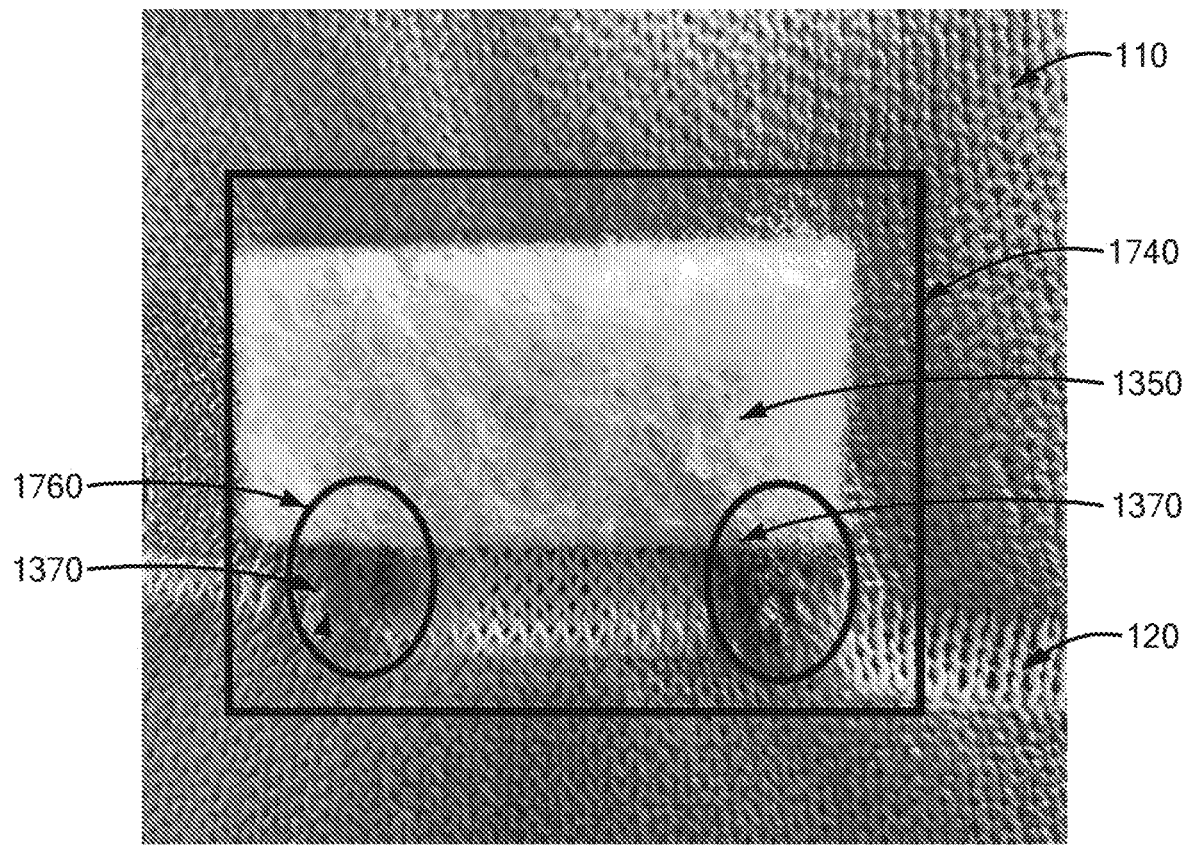
FIG. 10 is a photograph of an illustrative textile with a textile electrode connected to a conductive trace and covered by a piece of wool.

FIG. 10 is a photograph of an illustrative textile with a textile electrode connected to a conductive trace and covered by a piece of wool. FIG. 10 shows a section of a garment 100 with an integrated textile electrode region 130 connected to a conductive trace 120 and covered by a piece of reservoir material 1350 (shown here as a piece of felted natural wool). FIG. 10 shows the region around the textile electrode region 130 and reservoir material 1350, as well as a section of the conductive trace 120, to be sealed by the outer film 1340. FIG. 10 also shows the region 1760 around the two electrical contacts 1370 to be sealed by an inner film 1360.

Examples of Assembling a Moisture Retaining System

Figure 11:
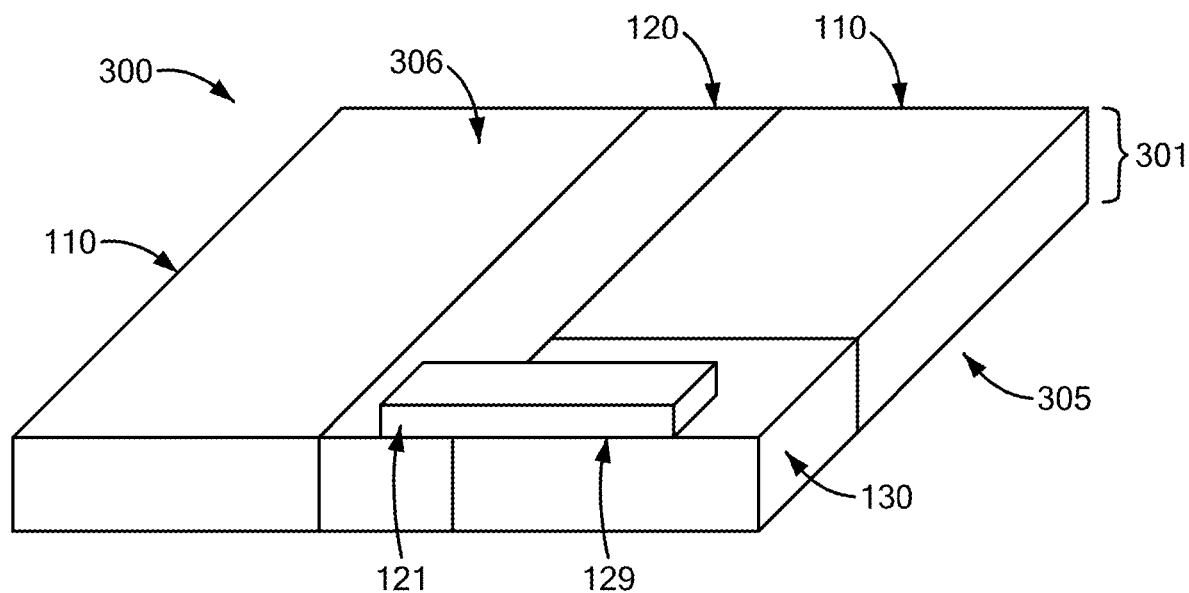
FIG. 11 is a schematic illustration of a single-layer of a continuous textile section knitted using the intarsia technique and having a conductive trace region passing through an inert region and across a face of an electrode region.

FIG. 11 is a schematic illustration of a single-layer of a continuous textile section 301 knitted using the intarsia technique and having a conductive trace region 120 passing through an inert region 110 and across a face of an electrode region 130. The conductive trace region 120 includes a knitted extension 121 that is knitted out of the single layer of the continuous textile section to form a second layer above the textile electrode region 130. This knitted extensions 121 of the conductive trace region 120 can be electrically connected with the textile electrode region 130 as discussed in FIGS. 12A-12E.

Figure 12A:
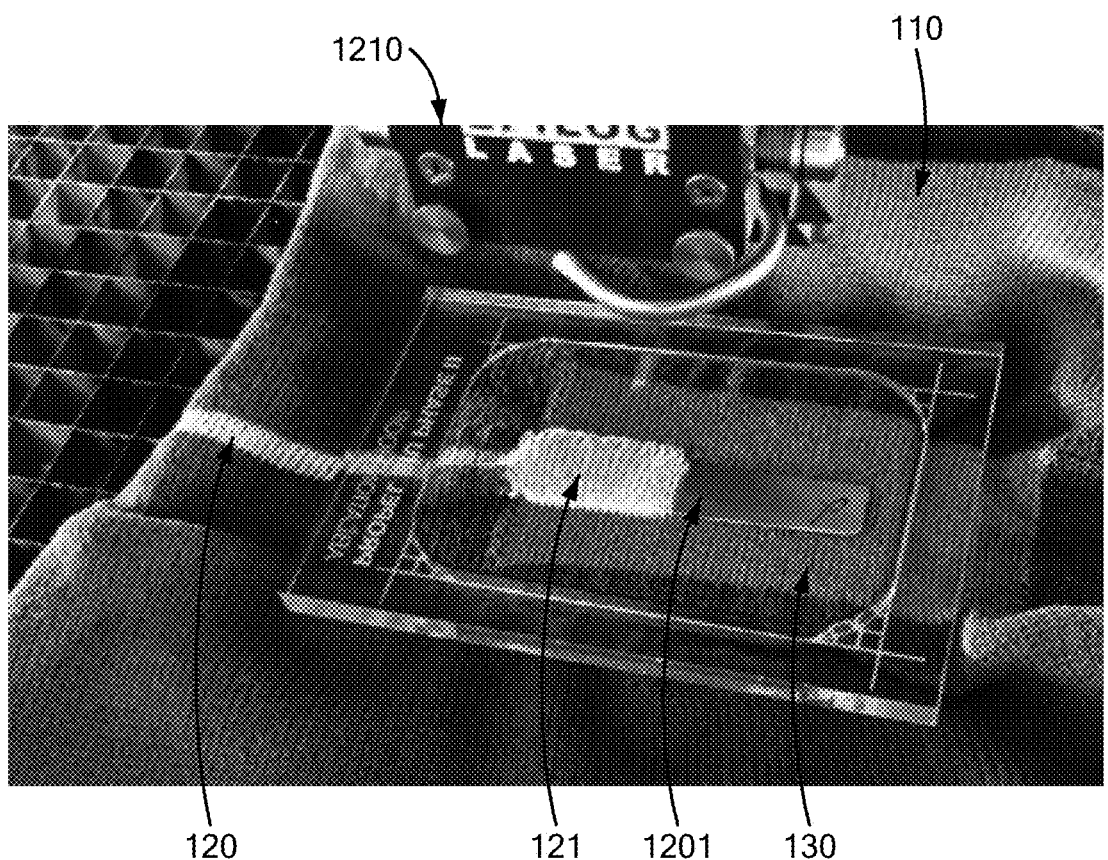
FIGS. 12A-12E are photographs of an embodiment of the steps for coupling a conductive trace region of a knitted textile to an integrated electrode region of the knitted textile by ablating a portion of the conductive trace region that extends across the integrated electrode.
Figure 12B:
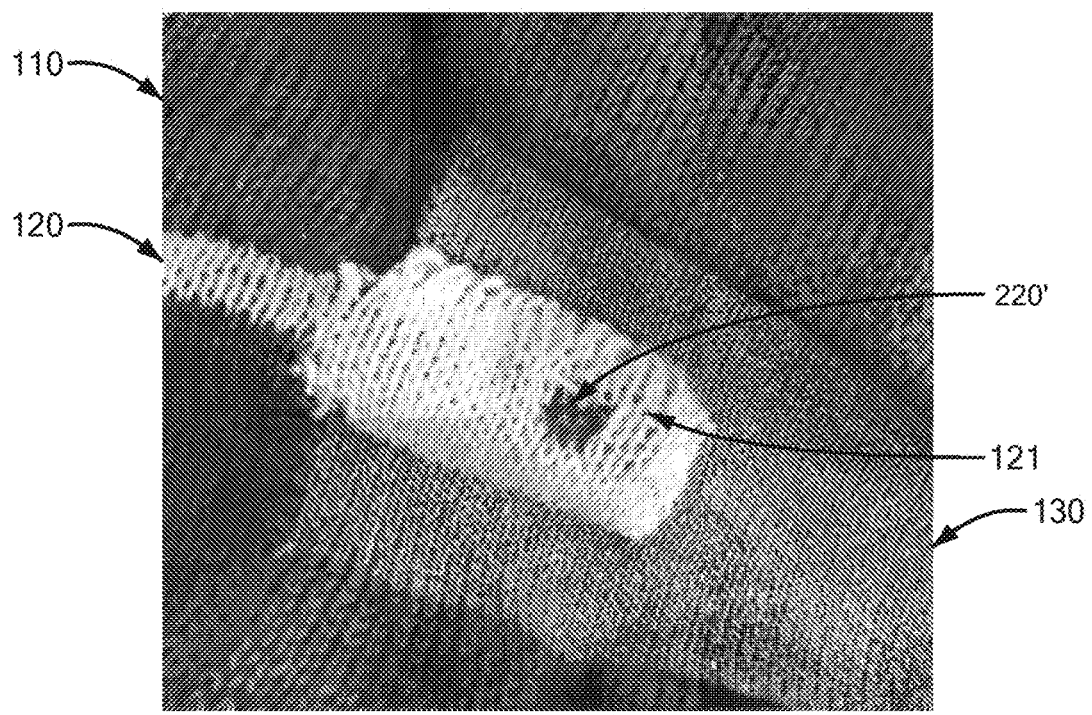
Figure 12C:
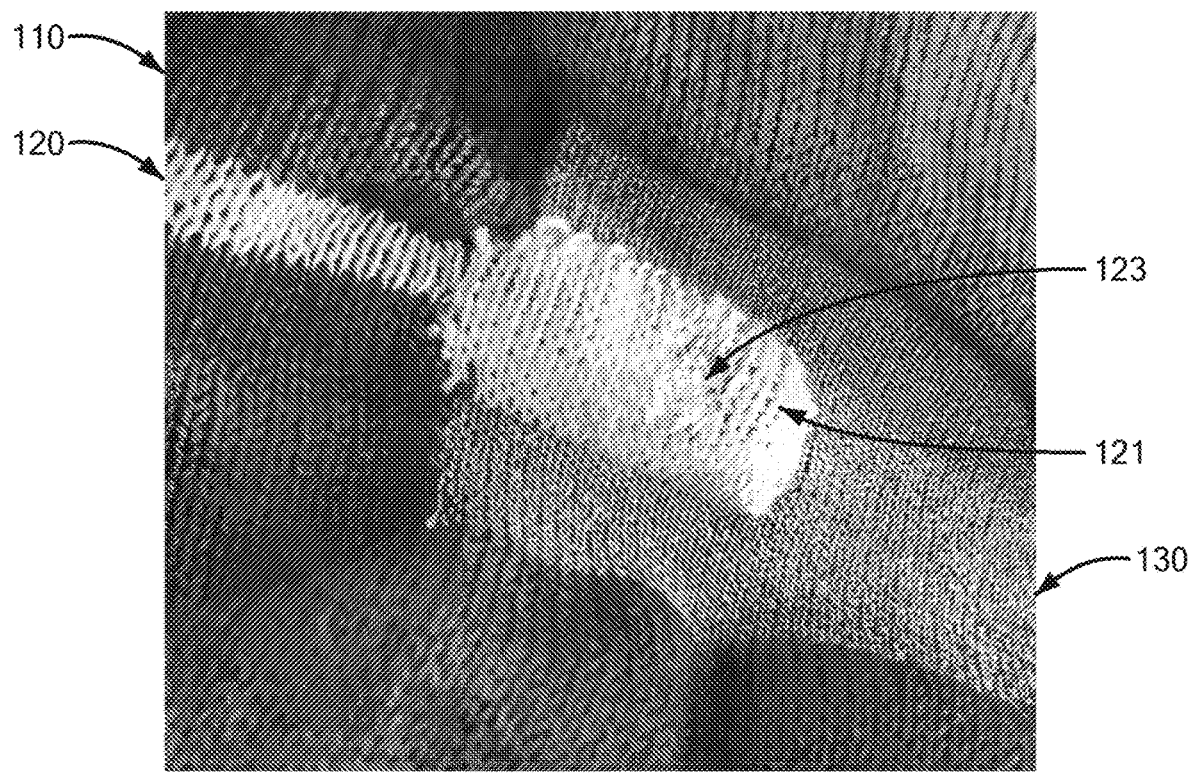
Figure 12D:
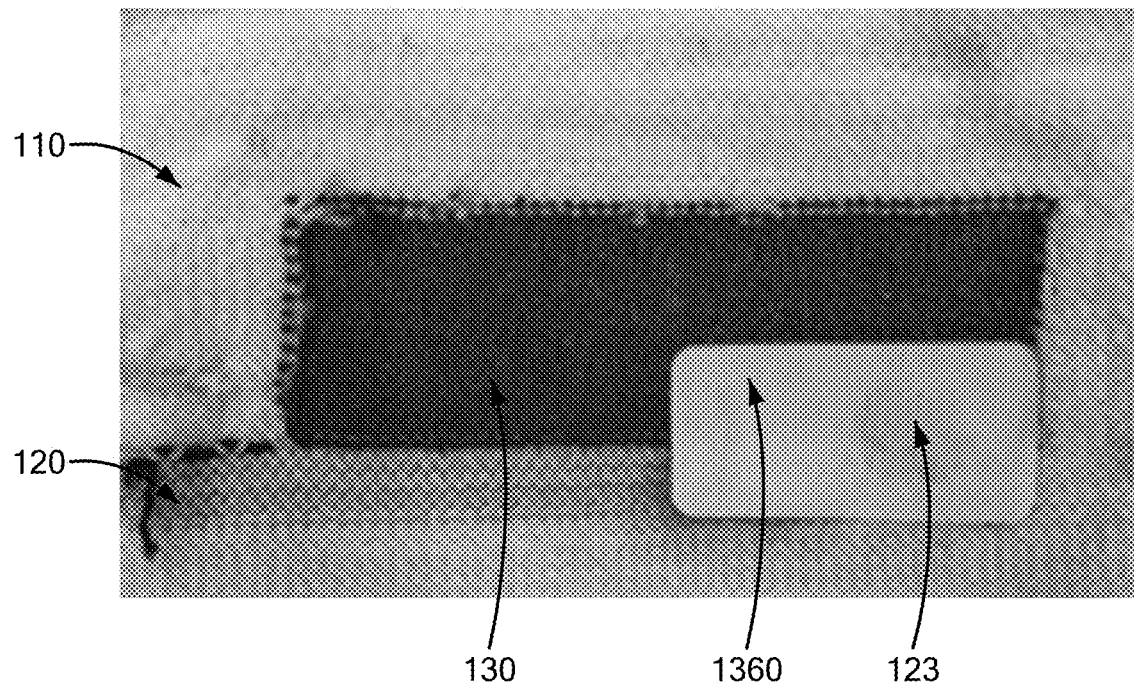
Figure 12E:
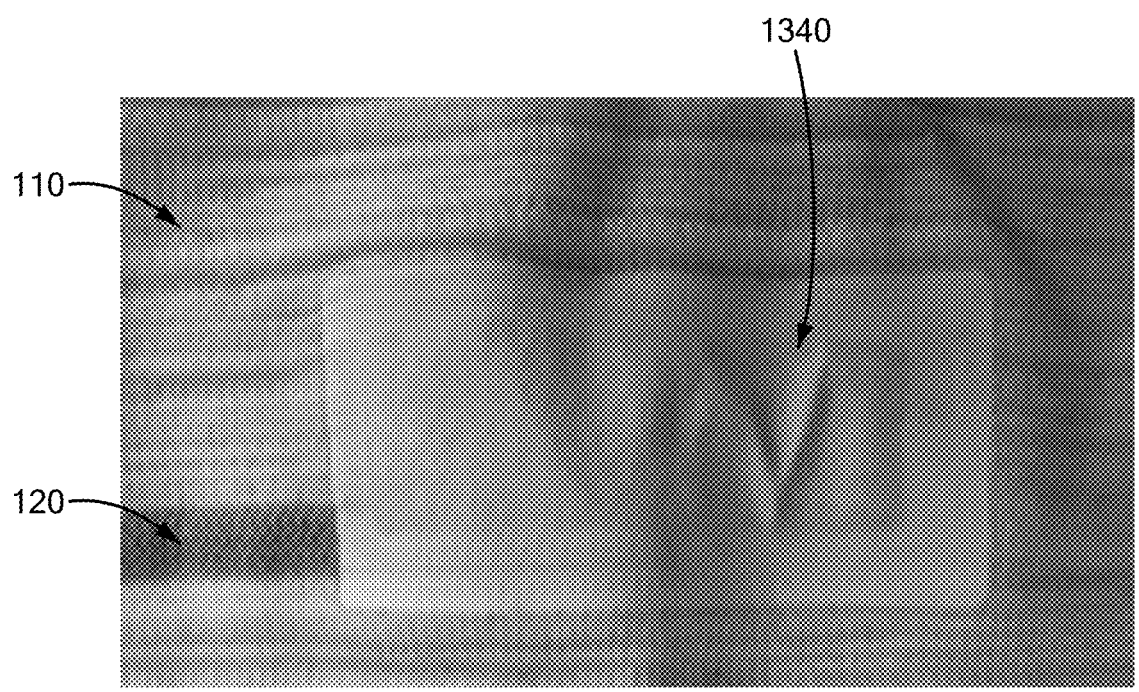

FIGS. 12A-12E are photographs of an embodiment of the steps for coupling a conductive trace region 120 of a knitted textile to an integrated textile electrode region 130 of the knitted textile by ablating a knitted extension 121 of the conductive trace region 120 that extends across the integrated electrode. In FIG. 12A, the textile section 301 of FIG. 11 is positioned below a laser ablation rig with a protective structure 1201 (e.g., a thin metal plate) disposed between the knitted extension 121 and the textile electrode region 130 to allow a portion of the knitted extension 121 to be ablated without damaging the textile electrode region 130. FIG. 12B shows the bare conductive wire 220' exposed in the portion of the knitted extension 121 that was ablated. In FIG. 12C, a conductive adhesive or similar conductive material 123 has been placed in and around the region of the knitted extension 121 with the bare conductive wire 220' to electrically connect the conductive wire 220 of the conductive trace region 120 with the textile electrode region 130. In FIG. 12D, a sealing film 1360 has been placed around the conductive material 123 to protect it and seal it from the surrounding textile layers 120, 130. In FIG. 12E, an outer sealing patch 1340 is placed around the entire textile electrode region 130 to create a moisture barrier between the textile electrode region 130 and the rest of the textile. In some instances, a reservoir material is also placed between the textile electrode region 130 and the outer sealing patch 1340 to retain moisture in the textile electrode region 130 and maintain the sensing performance of the textile electrode region 130 as the textile remains against the skin.

The embodiments of the invention described above are intended to be merely exemplary; numerous variations and modifications will be apparent to those skilled in the art. One skilled in the art will appreciate further features and advantages of the disclosure based on the above-described embodiments. Such variations and modifications are intended to be within the scope of the present invention as defined by any of the appended claims. Accordingly, the disclosure is not to be limited by what has been particularly shown and described, except as indicated by the appended claims. All publications and references cited herein are expressly incorporated herein by reference in their entirety.

What is claimed is:

1. A system for maintaining moisture in a textile electrode, the system comprising:
    a textile layer having a textile electrode region knitted therein and an insulated region adjacent to the textile electrode region, the textile electrode region and insulated region together defining a knitted continuous textile section, the textile layer having an inner side and an outer side opposite the inner side, the inner side of the textile electrode region being exposed and configured to contact against a user's skin;
    a reservoir positioned above the outer side of the textile electrode region;
    an outer sealing layer positioned above the reservoir, the outer sealing layer surrounding the reservoir and the textile electrode region,
    wherein the textile electrode region is knitted from an electrically conductive yarn having an exposed electrically conductive surface configured to permit water to migrate through the textile electrode region and into the reservoir, and
    wherein the insulated region is knitted from an electrically insulated or electrically inert yarn,
    the outer sealing layer configured to prevent water migration into the reservoir other than through the textile electrode region before entering the reservoir.

2. The system of claim 1,
    wherein the outer sealing layer extends through a thickness of the textile layer to the inner side of the textile layer.

3. The system of claim 2, wherein the outer sealing layer defines a moisture barrier around the textile electrode region and the reservoir and through the thickness of the textile layer around the textile electrode.

4. The system of claim 1, further comprising:
    an electrical contact between a conductive wire received through the outer sealing layer and the textile electrode.

5. The system of claim 4, further comprising:
    an inner sealing layer surrounding the electrical contact.

6. The system of claim 1,
wherein the outer sealing layer comprises an exterior film layer above the reservoir and the textile electrode region and an adhesive material securing the exterior film to the textile layer, and
wherein the adhesive material extends through the thickness of the textile layer to the inner side of the textile layer.

7. The system of claim 1,
wherein the insulated region comprises a conductive trace region knitted therein, the conductive trace region extending from a border of the textile electrode and through the outer sealing layer,
wherein the conductive trace region is knitted from a hybrid yarn containing a non-conductive yarn twisted with a conductive wire, the conductive wire having an exterior layer of an insulating material, and
wherein the textile electrode region is electrically connected to a conductive wire from the conductive trace region where the exterior layer is removed.

8. The system of claim 7,
wherein the insulated region comprises an electrical inert region, the conductive trace region extending through the electrically inert region, and
wherein the electrical inert region is knitted from an electrically inert yarn.

9. The system of claim 7,
wherein the textile layer having the textile electrode is a first layer, the system further comprising a second layer of the hybrid yarn knitted out of the conductive trace region and over a portion of the electrode region to form a two-layer section in the textile electrode region, and
wherein the exterior layer of the conductive wire of a portion of the conductive trace region in the two layer section is removed to expose a portion of the conductive wire and the exposed portion of the conductive wire is electrically connected with the electrode region via a conductive material.

10. The system of claim 9,
wherein the non-conductive yarn is removed where the exposed portion of the conductive wire is electrically connected with the electrode region.

11. The system of claim 9, further comprising:
an inner sealing layer surrounding the exposed portion of the conductive wire.

12. The system of claim 1,
wherein the reservoir comprises a skincore fiber having a hydrophilic or hygroscopic cortex and a hydrophobic exterior.

13. The system of claim 1, wherein the textile layer comprises a single knitted layer.

14. The system of claim 13, wherein the textile layer is knitting using intarsia knitting.

15. The system of claim 14, wherein the textile layer defines a garment.

16. The system of claim 15, wherein the electrode region is configured to pick up electrical signals from the user's body.

17. The system of claim 1, wherein the insulated region surrounds the textile electrode region.

18. A system for maintaining moisture in a textile electrode, the system comprising:
a textile layer having a textile electrode region knitted therein and an insulated region adjacent to the textile electrode region, the textile electrode region and insulated region together defining a knitted continuous textile section, wherein the knitted continuous textile section is knitted using an intarsia technique;
the textile layer having an inner side and an outer side opposite the inner side, the inner side of the textile electrode region being exposed and configured to contact against a user's skin;
a reservoir positioned above the outer side of the textile electrode region;
an outer sealing layer positioned above the reservoir, the outer sealing layer surrounding the reservoir and the textile electrode region,
wherein the textile electrode region is knitted from an electrically conductive yarn having an exposed electrically conductive surface configured to permit water to migrate through the textile electrode region and into the reservoir, and
wherein the insulated region is knitted from an electrically insulated or electrically inert yarn,
the outer sealing layer configured to prevent water migration into the reservoir other than through the textile electrode region before entering the reservoir.

19. The system of claim 18, wherein the outer sealing layer extends through a thickness of the textile layer to the inner side of the textile layer.

20. The system of claim 19, wherein the outer sealing layer defines a moistures barrier around the textile electrode region and the reservoir and through the thickness of the textile layer around the textile electrode.

21. The system of claim 1, wherein a conductive wire is connected to the textile electrode region with an electrical connection, wherein the electrical connection is encapsulated by an inner film that prevents moisture from the textile electrode region, the reservoir, or the user's skin from reaching the electrical connection.

22. The system of claim 18, wherein a conductive wire is connected to the textile electrode region with an electrical connection, wherein the electrical connection is encapsulated by an inner film that prevents moisture from the textile electrode region, the reservoir, or the user's skin from reaching the electrical connection.

* * * * *